United States Patent [19]

Kohl et al.

[11] Patent Number: 5,073,376

[45] Date of Patent: Dec. 17, 1991

[54] PREPARATIONS CONTAINING L-CARNITINE

[75] Inventors: Willibald E. Kohl, Muri bei Bern; Thomas Scholl, Visp, both of Switzerland

[73] Assignee: Lonza Ltd., Gampel, Switzerland

[21] Appl. No.: 499,629

[22] Filed: Mar. 27, 1990

[30] Foreign Application Priority Data

Dec. 22, 1989 [CH] Switzerland .......................... 4633/89

[51] Int. Cl.$^5$ ................................................ A61K 9/48
[52] U.S. Cl. .................................... 424/451; 424/464; 514/551; 514/556
[58] Field of Search ............... 424/451, 464, 465, 466, 424/440; 514/551, 556

[56] References Cited

U.S. PATENT DOCUMENTS

| | | | |
|---|---|---|---|
| 3,810,994 | 5/1974 | Wiegand | 424/316 |
| 4,255,449 | 3/1981 | Cavazza | 424/316 |
| 4,537,772 | 8/1985 | Alexander | 514/9 |

FOREIGN PATENT DOCUMENTS 57-126420  1/1981  Japan .................................. 514/556

*Primary Examiner*—Thurman K. Page
*Assistant Examiner*—D. Gabrielle Phelan
*Attorney, Agent, or Firm*—Fisher, Christen & Sabol

[57] ABSTRACT

Tablets, capsules and other preparation forms for oral administration are produced which contain L-carnitine-L-tartrate. In comparison to preparations made with free L-carnitine, the invention preparations exhibit less hygroscopicity, longer stability and better capacity for being stored.

10 Claims, No Drawings

PREPARATIONS CONTAINING L-CARNITINE

BACKGROUND OF THE INVENTION

1. Field Of The Invention

The invention relates to preparations containing L-carnitine for oral use in the form of tablets, capsules or powder.

2. Background Art

L-carnitine plays an important role in lipometabolism and is used especially in food for athletes, but also for the treatment of diseases with metabolic disorders. Athletic food preparations containing L-carnitine are widely used, since they contribute significantly to supplying the muscles with energy and promote endurance performance. Such preparations have great importance since they improve muscle activity and thereby bring about increased endurance and stress tolerance as well as delaying fatigue and shortening recovery time. However, the use of preparations containing L-carnitine is not limited to food for athletes, as they can also be used for geriatric purposes and as general food additives.

Thus, the application can basically take place both enterally and parenterally. For the preferred enteral, i.e., oral, application, suitable forms of administration, preferably in the form of tablets or capsules, optionally also in the form of powder or granulate, are thus necessary. Here the production takes place according to methods of pharmaceutical technology, independently of whether the form of administration is to serve for food purposes or therapeutic purposes. The production and handling of such forms of administration up to now have been made considerably more difficult because of the high hygroscopicity of L-carnitine. Thus, for example, tablets that contain L-carnitine must be produced with the exclusion of moisture and must be packaged hermetically and individually, since they would begin to liquefy in a short time even with the normal moisture in the air. Moreover, L-carnitine often contains traces of trimethylamine, which, because of its fishy odor, has a repulsive effect on the user.

BROAD DESCRIPTION OF THE INVENTION

The object of the invention is to make available a nonhygroscopic and odorless form of L-carnitine, which contains no physiologically unsafe additives and which is preferably suitable in particular for producing tablets or capsules.

According to the invention, the object is attained by the use of L-carnitine-L-tartrate for producing compositions for oral administration. Herein, L-carnitine-L-tartrate is to be understood as the salt of L-carnitine with L-tartaric acid in the molar ratio of 2:1.

It has been found that L-carnitine-L-tartrate at normal air moisture ($\leq 60$ percent relative humidity) is stable in storage and can be processed without special precautions. L-carnitine-L-tartrate forms a crystalline powder which can be easily processed and is particularly suitable for processing with rapidly running machines, since it does not tend to stick together or become lumpy. Moreover, it is completely odorless and because of the bonded tartaric acid it has a refreshing, somewhat acidic taste.

L-carnitine-L-tartrate is used advantageously alone or with additional active ingredients, such as, vitamins, amino acids, trace elements or mineral substances, as well as optionally the adjuvants usual for the respective form of administration. The forms of administration include particularly all kinds of tablets, both those that are swallowed without being chewed, and tablets to be chewed or sucked on, as well as those that are dissolved in a liquid before being taken. The tablet forms include uncoated tablets, in one-layer or multilayer or encased form, effervescent tablets, and coated tablets, such as, film tablets or dragees. Further preferred forms of administration are capsules of soft or hard gelatin. Of these, hard gelatin capsules in the form of hard-shell capsules are particularly preferred. Further, L-carnitine-L-tartrate can be used advantageously as a powder, for example, with gas-producing additives as an effervescent powder, or as granulated powder. Adjuvants are, for example, fillers, binding agents, lubricants and mold release agents, flow-regulating agents and disintegrants for the production of tablets, as well as coloring and flavoring substances. Such adjuvants are known to persons skilled in the art, as well as their use and the technology for producing the above-named forms of administration.

DETAILED DESCRIPTION OF THE INVENTION

The examples below explain the execution of the invention.

EXAMPLE 1

Production of L-carnitine-L-tartrate

L-tartaric acid was dissolved in the required quantity of hot 90 percent aqueous ethanol, the calculated quantity of L-carnitine was added, the salt was brought to crystallization by cooling, filtered and dried. The product showed the following characteristics: colorless crystals melting point: 169°–175° C.

$[a]_D^{25}$: $-10.9° \pm 0.6°$ (25° C., c=1% in water).

composition: mol ratio of carnitine: tartaric acid is 2:1 ($^1$H-NMR).

water solubility: about 73 g/100 g of solution.

water absorption when air humidity is 32 percent.

| After hours | L-carnitine-L-tartrate percent | L-carnitine percent |
|---|---|---|
| 1 | 0 | 1.9 |
| 2 | 0 | 3.6 |
| 4 | 0 | 6.3 |
| 8 | 0 | 8.6 |
| 24 | 0 | 12.3 |
| water absorption when air humidity is 66 percent | | |
| 1 | 0 | 6.0 |
| 2 | 0 | 9.6 |
| 4 | 0 | 21.6 |
| 8 | 0.1 | 45.2 |
| 24 | 0.1 | 67.7 |

EXAMPLE 2

Sucking Tablets With Orange Flavoring

Sucking tablets weighing individually 2,200 mg were produced according to the following formulation:

| | |
|---|---|
| L-carnitine-L-tartrate | 732 mg |
| fructose | 1,089 mg |
| orange flavoring | 30 mg |
| quinoline yellow lacquer | 4 mg |
| carboxymethyl cellulose | 25 mg |
| polyvinylpyrrolidone | 20 mg |
| saccharose stearate | 100 mg |

-continued

| | |
|---|---|
| talc | 160 mg |
| magnesium stearate | 40 mg |

The mixture was prepared in the usual manner and pressed into tablets 20 mm in diameter. As a comparison, sucking tablets of the same kind were produced which contained 500 mg of L-carnitine and 232 mg of microcrystalline cellulose (for weight compensation) instead of L-carnitine-L-tartrate. On the crushed tablets the water absorption in each case was determined under constant relativity humidity. When they were stored at a relative humidity of 56 percent the crushed tablets, which contained L-carnitine-L-tartrate, did not take up any water even after 10 days. In comparison to this, tablets that contained L-carnitine showed a water absorption of 12 percent under identical conditions. The use of L-carnitine-L-tartrate according to the invention resulted in tablets that could be stored even under extreme conditions.

EXAMPLE 3

Sucking Tablets With Peppermint Flavoring

Analogously to Example 2 sucking tablets were produced according to the following formulation:

| | |
|---|---|
| L-carnitine-L-tartrate | 732 mg |
| mannitol | 1,100 mg |
| aspartame | 13 mg |
| peppermint flavoring | 10 mg |
| carboxymethyl cellulose | 25 mg |
| polyvinyl pyrrolidone | 20 mg |
| saccharose stearate | 100 mg |
| talc | 160 mg |
| magnesium stearate | 40 mg |

As a comparison again as in Example 2, tablets were produced with L-carnitine and microcrystalline cellulose. Also with these tablets, as in Example 2, the water absorption was determined. The use according to the invention of L-carnitine-L-tartrate yielded stable tablets capable of being stored, while tablets on the basis of L-carnitine, after storage for one week, formed a sticky mass because of water absorption.

EXAMPLE 4

Tablets for Swallowing

According to the following formulation 12,000 tablets of 650 mg each were produced:

| | |
|---|---|
| L-carnitine-L-tartrate | 4.392 kg |
| lactose monohydrate (that can be directly tableted) | 2.028 kg |
| wheat starch | 420 g |
| cellulose, microcrystalline | 360 g |
| silicon dioxide (Aerosil ® 200) | 60 g |
| talc | 480 g |
| magnesium stearate | 60 g |

The L-carnitine-L-tartrate was homogeneously mixed with the wheat starch and the cellulose and sifted. The lactose was added, uniformly mixed in and the mixture was sifted again. Talc, magnesium stearate and silicon dioxide were thoroughly mixed with one another, sifted and sprinkled into the mixture of active ingredients. The whole mixture was again mixed thoroughly and kept in a hermetically sealed container until it was made into tablets. Circular tablets with a facette edge 13 mm in diameter and about 3.9 mm thick were pressed. The tablets exhibited a resistance to pressure of 60 to 70 N and disintegrated in water of 20° C. within 15 to 17 minutes.

EXAMPLE 5

Capsules for use as Food Supplement

Hard gelatin capsules with L-carnitine-L-tartrate were produced, corresponding to the following composition:

| | |
|---|---|
| L-carnitine-L-tartrate | 366 mg |
| magnesium stearate | 4 mg |

Magnesium stearate was sifted with a sieve with 0.5 mm mesh size, L-carnitine-L-tartrate was added, and both components were intensively mixed for 15 minutes. Afterwards the mixture was filled into CONI-SNAP ® capsules of size 1. This resulted in capsules that were capable of being stored even under tropical conditions. 366 mg of L-carnitine-L-tartrate per capsule corresponded to a quantity of 250 mg of L-carnitine.

We claim:

1. A preparation for enteral application comprising at least one tablet composed of the salt of L-carnitine with L-tartaric acid in the molar ratio of 2:1, powder composed of the salt of L-carnitine with L-tartaric acid in the molar ratio of 2:1 or at least one capsule containing the salt of L-carnitine with L-tartaric acid in the molar ratio of 2:1.

2. The preparation as claimed in claim 1 wherein said at least one tablet includes or said powder includes or at least one said capsule also contains at least one member of the group consisting of vitamin, amino acid, trace element, mineral substance, inert edible carrier or filler, gas-producing additive, disintegrant, binding agent, lubricant, mold release agent, flow regulating agent, colorant and flavorant, the at least one capsule being composed of soft or hard gelatin.

3. The preparation as claimed in claim 1 wherein the preparation is said at least one tablet.

4. The preparation as claimed in claim 3 wherein said at least one tablet includes a monosaccharide, a disaccharide, a sugar alcohol or a trisaccharide.

5. The preparation of claim 1 wherein the preparation is said powder.

6. The preparation as claimed in claim 1 wherein the preparation is said at least one capsule.

7. A process comprising preparing a preparation for oral administration, the preparation being composed of L-carnitine-L-tartrate, the L-carnitine-L-tartrate being the salt of L-carnitine with L-tartaric acid in the molar ratio of 2:1.

8. The process as claimed in claim 7 wherein the preparation is at least one tablet composed of L-carnitine-L-tartrate, and said process comprises tableting said L-carnitine-L-tartrate into at least one tablet.

9. The process as claimed in claim 7 wherein the preparation is at least one capsule containing L-carnitine-L-tartrate, and said process comprises placing said L-carnitine-L-tartrate into said at least one capsule.

10. Process comprising enterally consuming the preparation of claim 1 by a human.

* * * * *

/

(12) EX PARTE REEXAMINATION CERTIFICATE (4938th)
United States Patent
Kohl et al.

(10) Number: US 5,073,376 C1
(45) Certificate Issued: May 18, 2004

(54) PREPARATIONS CONTAINING L-CARNITINE

(75) Inventors: Willibald E. Kohl, Muri bei Bern (CH); Thomas Scholl, Visp (CH)

(73) Assignee: Lonza Ltd., Gampel/Valais (CH)

Reexamination Request:
No. 90/006,513, Jan. 13, 2003

Reexamination Certificate for:
Patent No.: 5,073,376
Issued: Dec. 17, 1991
Appl. No.: 07/499,629
Filed: Mar. 27, 1990

(30) Foreign Application Priority Data

Dec. 22, 1989 (CH) .................................. 4633/89

(51) Int. Cl.$^7$ .................. A61K 9/14; A61K 9/20; A61K 9/48
(52) U.S. Cl. .................. 424/451; 424/456; 424/464; 424/489; 514/551; 514/556

(56) References Cited

U.S. PATENT DOCUMENTS

| | | |
|---|---|---|
| 2,784,100 A | 3/1957 | Endicott |
| 3,359,119 A | 12/1967 | Milton |
| 3,480,185 A | 11/1969 | Steinberg |
| 3,653,914 A | 4/1972 | Schmitt |
| 4,172,072 A | 10/1979 | Ashmead |
| 4,267,163 A | 5/1981 | De Felice ............... 424/9 |
| 4,362,719 A | 12/1982 | Cavazza |
| 4,371,618 A | 2/1983 | Cavazza |
| 4,602,039 A | 7/1986 | Cavazza |
| RE32,398 E | 4/1987 | De Witt |
| 4,687,782 A | 8/1987 | Brantman |
| 4,753,804 A | 6/1988 | Iaccheri |
| 4,801,453 A | 1/1989 | Kosuge |
| 4,806,282 A | 2/1989 | Tinti |
| 4,855,289 A | 8/1989 | Wester |
| 4,871,550 A | 10/1989 | Millman |
| 4,883,786 A | 11/1989 | Puricelli |
| 4,895,980 A | 1/1990 | Walsdorf |
| 4,933,490 A | 6/1990 | Iannella |
| 4,968,517 A | 11/1990 | Gergely et al. ............. 426/285 |
| 4,968,719 A | 11/1990 | Brevetti ...................... 514/556 |
| 5,030,657 A | 7/1991 | Burtle |
| 5,071,874 A | 12/1991 | Scholl |

FOREIGN PATENT DOCUMENTS

| | | |
|---|---|---|
| DE | 23 217 | 1/1959 |
| DE | 93 347 | 10/1971 |
| DE | 93 347 | 10/1972 |
| DE | 31 49 517 A1 | 12/1981 |
| DE | 36 35 864 C2 | 10/1986 |
| EP | 0 076 340 | 8/1984 |
| EP | 0 150 688 | 8/1985 |
| EP | 0 434 088 A1 | 12/1990 |
| FR | 2 529 545 | 7/1982 |
| FR | 2 552 308 A1 | 9/1984 |

OTHER PUBLICATIONS

Muller, et al, Splitting of the Racemate of DL–Carnitine, Apr. 1972, Hoppe–Seyler's A. Physiol. Chem., vol. 353, pp. 618–622.*

Erich Struck and Irmgard Lorenz Bd. 318 (1960), pp. 120–137.

George D. Clayton and Florence E. Clayton, Toxicology, vol. 2.

Chem.Abstract, Choh Hao Li, Amino Acids, Peptides, and Proteins (1974).

Chem.Abstract No. 33996x, Aliphatics, vol. 77 (1972).

\* cited by examiner

*Primary Examiner*—James M. Spear

(57) ABSTRACT

Tablets, capsules and other preparation forms for oral administration are produced which contain L-carnitine-L-tartrate. In comparison to preparations made with free L-carnitine, the invention preparations exhibit less hygroscopicity, longer stability and better capacity for being stored.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–10 is confirmed.

\* \* \* \* \*